(12) United States Patent
Tao

(10) Patent No.: US 10,539,530 B2
(45) Date of Patent: Jan. 21, 2020

(54) SYSTEM AND METHOD FOR SMALL MOLECULE DETECTION

(71) Applicant: Nongjian Tao, Fountain Hills, AZ (US)

(72) Inventor: Nongjian Tao, Fountain Hills, AZ (US)

(73) Assignee: ARIZONA BOARD OF REGENTS, A BODY CORPORATE OF THE STATE OF ARIZONA ACTING FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 43 days.

(21) Appl. No.: 15/709,032

(22) Filed: Sep. 19, 2017

(65) Prior Publication Data

US 2018/0156752 A1    Jun. 7, 2018

Related U.S. Application Data

(63) Continuation of application No. 13/613,672, filed on Sep. 13, 2012, now Pat. No. 9,772,305.
(Continued)

(51) Int. Cl.
| | |
|---|---|
| *G01N 27/60* | (2006.01) |
| *B82Y 35/00* | (2011.01) |
| *G01B 11/00* | (2006.01) |
| *G01N 15/06* | (2006.01) |
| *G01N 33/00* | (2006.01) |

(52) U.S. Cl.
CPC ............. *G01N 27/60* (2013.01); *B82Y 35/00* (2013.01); *G01B 11/002* (2013.01)

(58) Field of Classification Search
CPC ........ G01N 15/06; G01N 33/00; G01N 33/48; G01N 35/00; G01N 21/01; G01N 21/00; G01N 27/60; B82Y 35/00; G01B 11/002

USPC .......... 422/68.1, 82.01, 82.02, 82.05, 82.06; 436/43, 149, 164, 165, 166, 172
See application file for complete search history.

(56) References Cited

U.S. PATENT DOCUMENTS

| | | | | |
|---|---|---|---|---|
| 4,743,116 A | * | 5/1988 | Udd .................... | G01C 19/72 250/227.12 |
| 4,897,541 A | * | 1/1990 | Phillips .................. | G01D 5/268 250/227.21 |

(Continued)

FOREIGN PATENT DOCUMENTS

| | | |
|---|---|---|
| EP | 2017612 A1 | 1/2009 |
| WO | 2004042403 A3 | 7/2004 |
| WO | 2008033167 A3 | 3/2008 |

OTHER PUBLICATIONS

Reimer, Charles B., et al., "Influenza virus purification with the zonal ultracentrifuge," Science, Jun. 3, 1966, pp. 1379-1381, vol. 152, No. 727.

(Continued)

*Primary Examiner* — Brian J. Sines
(74) *Attorney, Agent, or Firm* — Quarles & Brady LLP; Jessica L. Lewis

(57) ABSTRACT

A system for analyzing a content of a sample material is presented. The system includes a fiber sensitized to a first substance, and at least one electrode configured to expose the fiber to an electric field. The system includes an optical sensor configured to detect a displacement of the fiber when the fiber is exposed to the electric field, and a processor configured to use the displacement of the fiber to characterize a content of the sample material.

12 Claims, 5 Drawing Sheets

Related U.S. Application Data

(60) Provisional application No. 61/535,231, filed on Sep. 15, 2011.

(56) References Cited

U.S. PATENT DOCUMENTS

| | | | |
|---|---|---|---|
| 6,503,711 B1 * | 1/2003 | Krull | C12Q 1/6825 |
| | | | 250/458.1 |
| 6,743,581 B1 * | 6/2004 | Vo-Dinh | C12Q 1/001 |
| | | | 356/335 |
| 6,867,865 B2 | 3/2005 | Vaupel | |
| 7,150,978 B2 | 12/2006 | Yanagawa | |
| 7,364,919 B2 | 4/2008 | Penades | |
| 7,900,527 B1 | 3/2011 | Su | |
| 8,252,598 B2 | 8/2012 | Koley | |
| 8,416,417 B2 | 4/2013 | Tao | |
| 9,772,305 B2 * | 9/2017 | Tao | G01N 27/60 |
| 2006/0075803 A1 | 4/2006 | Boisen | |
| 2007/0178534 A1 * | 8/2007 | Murphy | B82Y 15/00 |
| | | | 435/7.2 |
| 2007/0281322 A1 * | 12/2007 | Jaffe | G01J 3/10 |
| | | | 435/7.1 |
| 2008/0043222 A1 | 2/2008 | Miller | |
| 2008/0285040 A1 | 11/2008 | Fourkas | |
| 2011/0140706 A1 | 6/2011 | Groves | |
| 2012/0327959 A1 * | 12/2012 | Fermann | H01S 3/08059 |
| | | | 372/6 |

OTHER PUBLICATIONS

Kretschmann, Erwin et al., "The Determination of the Optical Constants of Metals by Excitation of Surface Plasmons," Z. Physik, 1971, pp. 313-324, vol. 241.
McIntyre, J.D.E., "Electrochemical Modulation Spectroscopy," Surf. Sci., 1973, pp. 658-682, vol. 37, No. 1.
Orlowski, R., et al., "The Total Reflection of Light at Smooth and Rough Silver Films and Surface Plasmons," Suf. Sci., 1976, pp. 303-308, vol. 54, No. 2.
Kotz, R., et al., "Electron Density Effects in Surface Plasmon Excitation on Silver and Gold Electrodes," Surf. Sci., 1977, pp. 359-364, vol. 69, No. 1.
Hart, Helena, et al., "Association of human cytomegalovirus (HCMV) with mink and rabbit lung cells," Arch. Virol. , 1981, pp. 203-215, vol. 67, No. 3.
Hamelin, A, et al., "The Electrochemical Double Layer on sp Metal Single Crystals," J. Electroanal. Chem., 1983, pp. 225-264, vol. 145, No. 2.
Porter, Marc D., et al., "Spontaneously Organized Molecular Assemblies. 4. Structural Characterization of n-Alkyl Thiol Monolayers on Gold by Optical Ellipsometry, Infrared Spectroscopy, and Electrochemistry," J. Am. Chem. Soc., 1987, pp. 3559-3568, vol. 109, No. 12.
Kumar, Amit, et al., "Patterning Self-Assembled Monolayers: Applications in Materials Science," Langmuir, 1994, pp. 1498-1511, vol. 10.
Peterlinz, Kevin A., et al., "In Situ Kinetics of Self-Assembly by Surface Plasmon Resonance Spectroscopy," Langmuir, Oct. 1996, pp. 4731-4740, vol. 12, No. 20.
Tao, N.J., et al., "High resolution surface plasmon resonance spectroscopy," Rev. Sci. Instrum., Dec. 1999, pp. 4656-4660, vol. 70, No. 12.
Barrena, E. et al., "Molecular packing changes of alkanethiols monolayers on Au(111) under applied pressure," J. Chem. Physics, Aug. 8, 2000, pp. 2413-2418, vol. 113, No. 6.
He, Lin, et al., "Colloidal Au-Enhanced Surface Plasmon Resonance for Ultrasensitive Detection of DNA Hybridization," J. Am. Chem. Soc., 2000, pp. 9071-9077, vol. 122, No. 38.
Wang, S., et al., "High-Sensitivity Stark Spectroscopy Obtained by Surface Plasmon Resonance Measurement," Anal. Chem., Sep. 1, 2000, pp. 4003-4008, vol. 72, No. 17.

Arntz, Y. et al., "Label-free protein assay based on a nanomechanical cantilever array," Nanotechnology, Institute of Physics Publishing, 2003, pp. 86-90, vol. 14.
Katz, Eugenii, et al., "Probing Biomolecular Interactions at Conductive and Semiconductive Surfaces by Impedance Spectroscopy: Routes to Impedimetric Immunosensors, DNA-Sensors, and Enzyme Biosensors," Electroanal., Jul. 2003, pp. 913-947, vol. 15, No. 11.
Voros, Janos, "The density and refractive index of adsorbing protein layers," Biophys. J., Jul. 2004, pp. 553-561, vol. 87, No. 1.
Patolsky, F., et al., "Electrical detection of single viruses," PNAS, Sep. 28, 2004, pp. 14017-14022, vol. 101, No. 39.
Sheehan, P.E., et al, "Detection limits for nanoscale biosensors," Nano Lett., 2005, pp. 803-807, vol. 5, No. 4.
Yang, Y.T., et al., "Zeptogram-scale nanomechanical mass sensing," Nano Lett., Apr. 2006, pp. 583-586, vol. 6, No. 4.
Jin, Y.L., et al., "Refractive index measurement for biomaterial samples by total internal reflection," Phys. Med. Biol., 2006, pp. N371-N379, vol. 51, No. 20.
Campbell, Charles T., et al., "SPR microscopy and its applications to high-throughput analyses of biomolecular binding events and their kinetics," Biomaterials, 2007, pp. 2380-2392, vol. 28, No. 15.
Huang, Bo, et al., "Surface plasmon resonance imaging using a high numerical aperture microscope objective," Anal. Chem., Apr. 1, 2007, pp. 2979-2983, vol. 79, No. 7.
Brandenburg, Boerries., et al., "Imaging poliovirus entry in live cells," PLoS Biol., Jul. 2007, p. e183, vol. 5, No. 7.
Armani, Andrea M., et al., "Label-free, single-molecule detection with optical microcavities," Science, Aug. 10, 2007, pp. 783-787, vol. 317.
Homola, Jiri, "Surface plasmon resonance sensors for detection of chemical and biological species," Chem. Rev., 2008, pp. 462-493, vol. 108.
Le, Thu Tran, et al., "Determination of heat-induced effects on the particle size distribution of casein micelles by dynamic light scattering and nanoparticle tracking analysis," Int. Dairy J., 2008, pp. 1090-1096, vol. 18.
Yang, Wenrong R., et al., "Single Molecule Conductance through Rigid Norbornylogous Bridges with Zero Average Curvature," J. Phys. Chem. C., 2008, pp. 9077-9080, vol. 112, No. 24.
Yao, Jimin, et al., "Seeing molecules by eye: Surface plasmon resonance imaging at visible wavelengths with high spatial resolution and submonolayer sensitivity," Angew. Chemie Int. Ed., 2008, pp. 5013-5017, vol. 47.
Vollmer, F. et al., "Single virus detection from the reactive shift of a whispering-gallery mode," PNAS, Dec. 30, 2008, pp. 20701-20704, vol. 105, No. 52.
Naik, A.K., et al., "Towards single-molecule nanomechanical mass spectrometry," Nat. Nanotechnol., Jul. 2009, pp. 445-450, vol. 4, No. 7.
Zhu, Jiangang, et al., "On-chip single nanoparticle detection and sizing by mode splitting in an ultrahigh-Q microresonator," Nat. Photonics, Jan. 2010, pp. 46-49, vol. 4.
Cipriany, Benjamin R., et al., "Single molecule epigenetic analysis in a nanofluidic channel," Anal. Chem., Mar. 15, 2010, pp. 2480-2487, vol. 82, No. 6.
Wang, Shaopeng, et al., "Label-free imaging, detection, and mass measurement of single viruses by surface plasmon resonance," PNAS, Sep. 14, 2010, pp. 16026-16032, vol. 107, No. 37.
Ozkumur, Emre, et al. "Spectral Reflectance Imaging for a Multiplexed, High-Throughput, Label-Free, and Dynamic Biosensing Platform," 2010 IEEE J Sel Topics in Quantum Electronics, vol. 16, No. 3, May/Jun. 2010.
Ozkumur, Emre, et al. "Label-Free and Dynamic Detection of Biomolecular Interactions for High-Throughput Microarray Applications" 2008 PNAS, Jun. 2008, pp. 7988-7992, vol. 105 No. 23.
International Search Report for PCT application No. PCT/US2009/041648 published Jun. 24, 2009, 3 pages.
International Preliminary Report on Patentability for PCT application No. PCT/US2009/041648 dated Oct. 26, 2010.
Gaillard, Jay, "Harmonic Detection of Resonance in Micro- and -Nano Cantilevers," Thesis, Clemson University, 2006, pp. 1-121.

(56) References Cited

OTHER PUBLICATIONS

Zeltzer, G. et al. "Scanning optical homodyne detection of high-frequency picoscale resonances in cantilever and tuning fork sensors," Appl. Phys. Lett., 2007, v. 91, 173124, pp. 1-3.
Obukhov, Yu et al. "Realtime cantilever signal frequency determination using digital signal processing," J. Appl. Phys., 2007 v. 101, 034315 pp. 1-5.

* cited by examiner

SYSTEM AND METHOD FOR SMALL MOLECULE DETECTION

CROSS-REFERENCE TO RELATED APPLICATIONS

This application claims priority to U.S. application Ser. No. 13/613,672 filed on Sep. 13, 2012, which claims the benefit of U.S. provisional Application No. 61/535,231 filed on Sep. 15, 2011, both of which are incorporated by reference herein in their entirety.

BACKGROUND OF THE INVENTION

The analysis of both the molecular composition and molecular activity within a particular substance is important in many different applications, including the detection of biomarkers for disease diagnosis and DNA sequencing, drug discovery and screening, and immunosignaturing, which involves detecting the changes of human antibodies.

One conventional system for detecting particular molecules within a substance involves introducing a fluorescent dye molecule into a particular sample. The dye marker is configured to bind to the molecules of interest, if present, within the sample. After introduction of the dye molecule, the sample is irradiated using ultraviolet (UV) radiation, which causes dye molecules that have bonded to the target molecule to fluoresce. If the sample fluoresces, that fluorescence indicates that the molecule of interest is present within the sample. Generally, sensitive optical instruments are used to monitor the sample for fluorescence and, thereby, identify the presence of the molecule of interest.

These fluorescence-based detection systems suffer from a number of drawbacks. First, the systems require UV light sources and highly sensitive optical detectors to detect the weak fluorescent light emission from a sample. This equipment can be very expensive and bulky. Additionally, when attempting to detect small molecules, the fluorescent dye molecule often alters the native properties of molecules of interest, rendering test results inaccurate and of little value. Finally, fluorescence detection is only useful as an end-point test and cannot be used to study the kinetics of molecular interactions and binding processes.

In response to the difficulties associated with fluorescent label analysis and other label analysis methods, label-free, optical detection technologies have been developed. One such method involves the analysis of data captured from the excitation of surface plasmons in a sample material. The instrumentation required to perform such surface plasmon resonance (SPR), however, is bulky and expensive due to the need of complex optics. This system also requires the fabrication of SPR chips (gold-coated glass chips), which is expensive and difficult.

Another label-free detection method relies upon detecting light interference created by a structured surface (e.g., multiple layer coating of chips) over which a sample is deposited. Although this approach may be somewhat simpler than SPR, it is also less sensitive than SPR. In some cases, to improve sensitivity, deep microstructures are etched onto a silicon chip to increase the surface area of the chip. This approach, therefore, introduces additional fabrication steps into the analysis process. Additionally, these microstructures can affect the molecule binding kinetics because, prior to binding, the molecules must diffuse into the constricted spaces defined by the microstructures.

The non-label, optical approaches called for in both SPR and interference-based analysis are all based upon measuring the optical mass of particular molecules. Because the optical mass of a molecule is proportional to the size of the molecule, these analysis techniques are not effective for detecting small molecules.

Another alternative for the molecular analysis of a sample involves the use of Microfabricated Electromechanical System devices (MEMS), such as cantilevers, tuning forks and quartz-crystal resonators, which can each be used for label-free detection of mass and spring constant changes associated with molecular binding events. In many cases, though, viscous damping of these mechanical devices, resulting from their placement within a sample aqueous solution, severely limits the ability of such systems to make accurate measurements. Additionally, the fabrication of MEMS devices requires microfabrication and cleanroom facilities, which are labor-intensive and expensive. Finally, these MEMs devices also have difficultly in detecting small molecules.

DETAILED DESCRIPTION OF THE INVENTION

The present system relates to the analysis of sample material to identify the presence of target molecules. To detect and/or identify the target molecules, the present system measures a deflection of a mechanically bendable microfiber that is sensitized to a particular target molecule. The fiber is brought into contact with the sample. As the target molecules in the sample interact with the microfiber, an electric charge is developed upon the surface of the microfiber. By subjecting the charged microfiber to an electrical field, and measuring the subsequent deflection of the charged microfiber due to the application of the electric field, the present system can identify the presence or absence of the target molecule within the sample.

In contrast to conventional detection methods and system, the present system allows for the detection of relatively small molecules without modifying their chemical structure by labeling, which might otherwise invalidate measurement results. Instead, the system exploits the conversion of molecular binding-induced charge changes into a mechanical deflection of a flexible fiber. That deflection can then be detected optically, or by another suitable detection mechanism. The present system can be used with existing microplate technology in combination with an optical microscope, for example.

Figure 1:
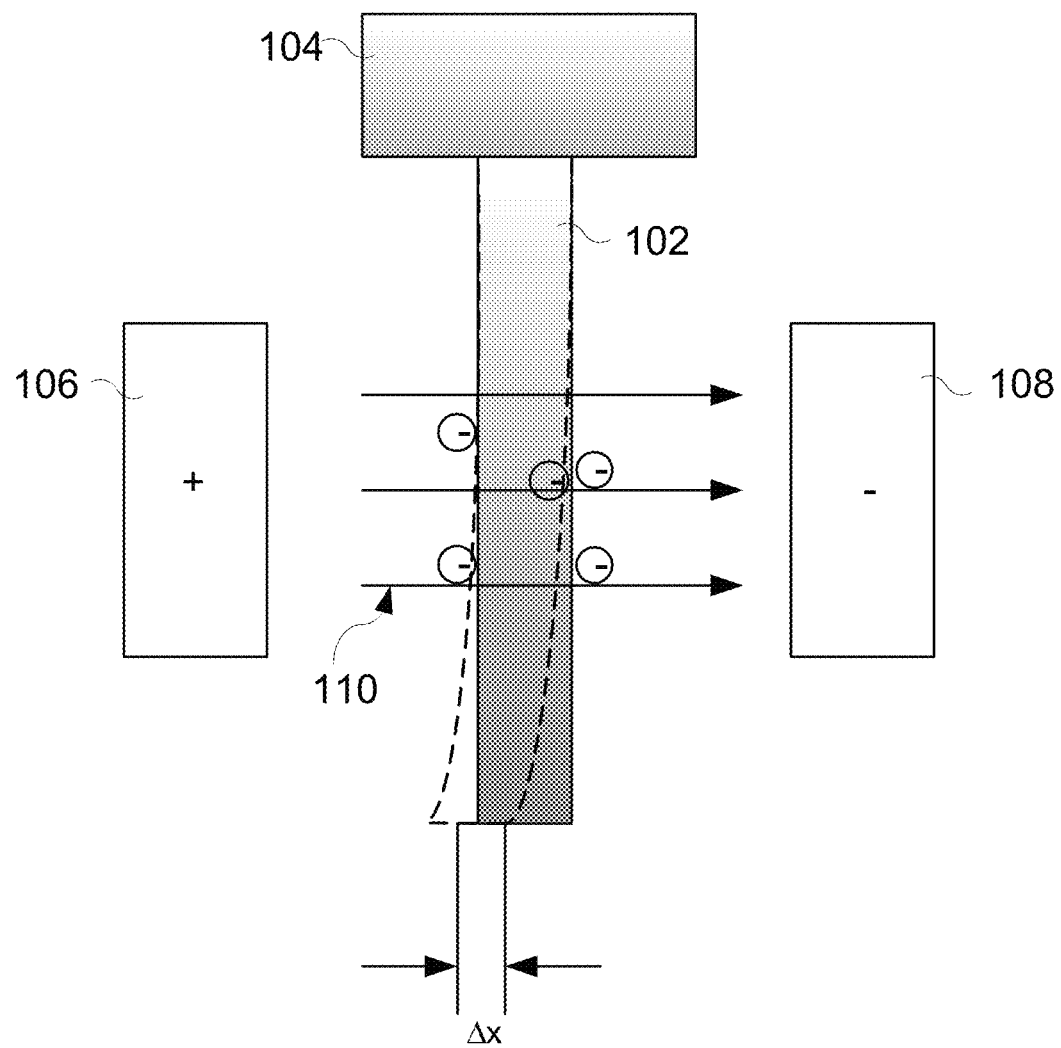
FIG. 1 is a schematic illustrating some of the functional components of the present analysis system.

FIG. 1 is a schematic illustrating some of the functional components of the present analysis system 100. System 100 includes fiber 102 that is connected to mechanical support 104. Fiber 102 is sensitized so that a surface of fiber 102, or a material disposed over a surface of fiber 102, will interact with a particular type of target molecule, such as particular analytes, enzymes, or other chemical species. As the target molecules interact with fiber 102 or the coating formed thereover, an electrical charge (either positive or negative) is built-up along the surface of fiber 102.

Fiber 102 may include a single glass fiber connected to support 104. Alternatively, fiber 102 may include several independent filaments that are each bundled together, with the bundle being connected to support 104. In a multiple-filament implementation, each filament of the bundle may be of the same construction and chemical make-up. Alternatively, several of the filaments contained within the bundle may comprise different materials, or be sensitized to different target molecules.

The fiber in the system could include one or more optical glass fibers that are mass-produced and widely used in optical communications. Such glass fibers are uniform, high quality, and low cost. The glass fibers can also be prepared by heating and pulling glass rods or tubing. Commercial apparatus for preparing such glass fibers are available. The fiber material is not limited to glass. Carbon fibers are also widely available and can be used in the present system. Furthermore, metal wires can also serve as the fiber.

System 100 includes electrodes 106 and 108, which can be positioned on either side of fiber 102. As electrodes 106 and 108 are energized by an appropriate input signal, electric field 110 is generated in a direction that is substantially perpendicular to the length of fiber 102. Although FIG. 1 shows two electrodes 106 and 108, in other implementations, electrodes 106 and 108 may be replaced with other systems or devices for applying an electric field to fiber 102.

In one example use of system 100, fiber 102 is first exposed to a particular sample material, for example by dipping, or positioning fiber 102 within a solution well containing the sample material. If the sample material contains molecules to which fiber 102 has been sensitized, the molecules interact with fiber 102 (or a surface coating thereof) causing an electrical charge to build-up on the surface of fiber 102. The charged fiber 102 is then subjected to electric field 110. Electric field 110 applies an electric force and, consequently, a mechanical force to the charged fiber 102, which causes fiber 102 to become displaced. That displacement can then be measured making it possible to quantify an amount of built-up charge on fiber 102, which, in turn, can be used to identify an amount of interaction between fiber 102 and molecules contained within the sample material.

In system 100, the magnitude of electric field 110 is defined as E, and the charge change of fiber 102 due to interactions with the target molecules is defined as $\Delta q$. The spring constant of fiber 102 (for lateral movement within field 110) is defined as k. Finally, the displacement of the tip of fiber 102 is defined as $\Delta x$, as shown in FIG. 1, where the dashed outline shows the position of fiber 102 after displacement.

Using these values, the charge build-up on fiber 102 ($\Delta q$) can be related to the change in position of fiber 102 in electric field 110 in accordance with equation (1).

$$E\Delta q = k\Delta x \qquad \text{Equation (1)}$$

Thus, it is possible to determine the amount of displacement of fiber 102 $\Delta x$ as shown in equation (2).

$$\Delta x = \frac{E}{k}\Delta q \qquad \text{Equation (2)}$$

In equations (1) and (2), both k and E can be determined either experimentally or calculated theoretically, and $\Delta q$ can be determined after $\Delta x$ is measured. In circumstances where the amount of charge change $\Delta q$ is relatively small, the resulting movement ($\Delta x$) of fiber 102 can be amplified by using a softer or more flexible fiber 102 having a lower spring constant k. The charge change $\Delta q$ can then be used to characterize the chemical reaction between the sensitized fiber 102 and molecules within the sample material.

At a given pH and buffer concentration, the amount of charge change $\Delta q$ is directly proportional to the number of target molecules interacting with fiber 102. Accurate detection of the charge change $\Delta q$ provides quantitative measurement of the molecules. For example, in the case of phosphorylation or DNA, each phosphorylation or DNA base corresponds to a fixed amount of charge. As such, it is also possible to detect the sign (positive vs. negative) of the charge, which leads to additional information about the nature of the target molecules. The amount of charge can be enhanced by optimizing the pH and buffer concentration to achieve the best detection limit.

The accuracy of system 100 can also be increased by increasing the strength of electric field 110 E while also minimizing the strength (i.e., spring constant k) of fiber 102. By both increasing the strength of electric field E and decreasing the lateral spring constant k of fiber 102, the amount of lateral deflection of fiber 102 $\Delta x$ for a given charge build-up $\Delta q$ is increased, making detection of the displacement (and, consequently, relatively small amounts of charge build-up) easier. Accordingly, for low-levels of charge build-up $\Delta q$, a relatively high electric field E in combination with a flexible fiber 102 allows for accurate detection of the presence of target molecules within a sample. The detection limits of the present system are, however, limited. Generally, a practical limit for decreasing the spring constant of fiber 102 is that of Brownian motion or thermal fluctuations in the fiber 102's displacement. That displacement is given by equation (3).

$$(\Delta x)_T = (k_B T/k)^{1/2} \qquad \text{Equation (3)}$$

In equation (3), $k_B = 1.38 \times 10^{-23}$ J/K and T is temperature. Equation (3) illustrates that when optimizing the present system by tuning the spring constant of fiber 102, the thermal noise described by equation (3) can be accounted for.

In some applications, the system is optimized to detect surface charge density, or charge per unit area on fiber 102, rather than total amount of charge accumulated on fiber 102. This is because the surface charge density may be more closely related to the concentration of analytes. As the surface charge density is determined by the total charge divided by the surface area and the spring constant k of fiber 102 (both values that are determined by the geometry of fiber 102), appropriate selection of the dimensions of fiber 102 can lead to improved detection limits (e.g., sensitivity) for surface charge or charge per unit area.

The detection limit of the present system may also be improved by applying a modulated electric field to electrodes 106 and 108 (or other electric field-generating devices of system 100) with an appropriate frequency. The frequency range can be varied from a few Hz to a few MHz, depending upon the mechanical properties of the fibers and optical detection response time. After subjecting fiber 102 to that modulated field, the displacement of the tip of fiber 102 can then be monitored by an optical sensor, such as a CCD or CMOS sensor. By observing the movement of fiber 102 over time, and performing a Fourier transform of the time profile, displacement of fiber 102 at the frequency of the applied electric field can be isolated. By isolating the displacement of fiber 102 due directly to the electric field, noises at other frequencies can be removed from the observed data allowing for more accurate tracking of fiber 102.

There are a number of different ways to measure the mechanical bending of fiber 102. Mechanical sensors, such as pressure sensors, disposed within support 104 may be configured to detect a flexing or movement of fiber 102. Alternatively, optical sensors may be used to detect a movement of fiber 102 by comparing a position of fiber 102 before and after exposure of an electrical field.

Figure 2:
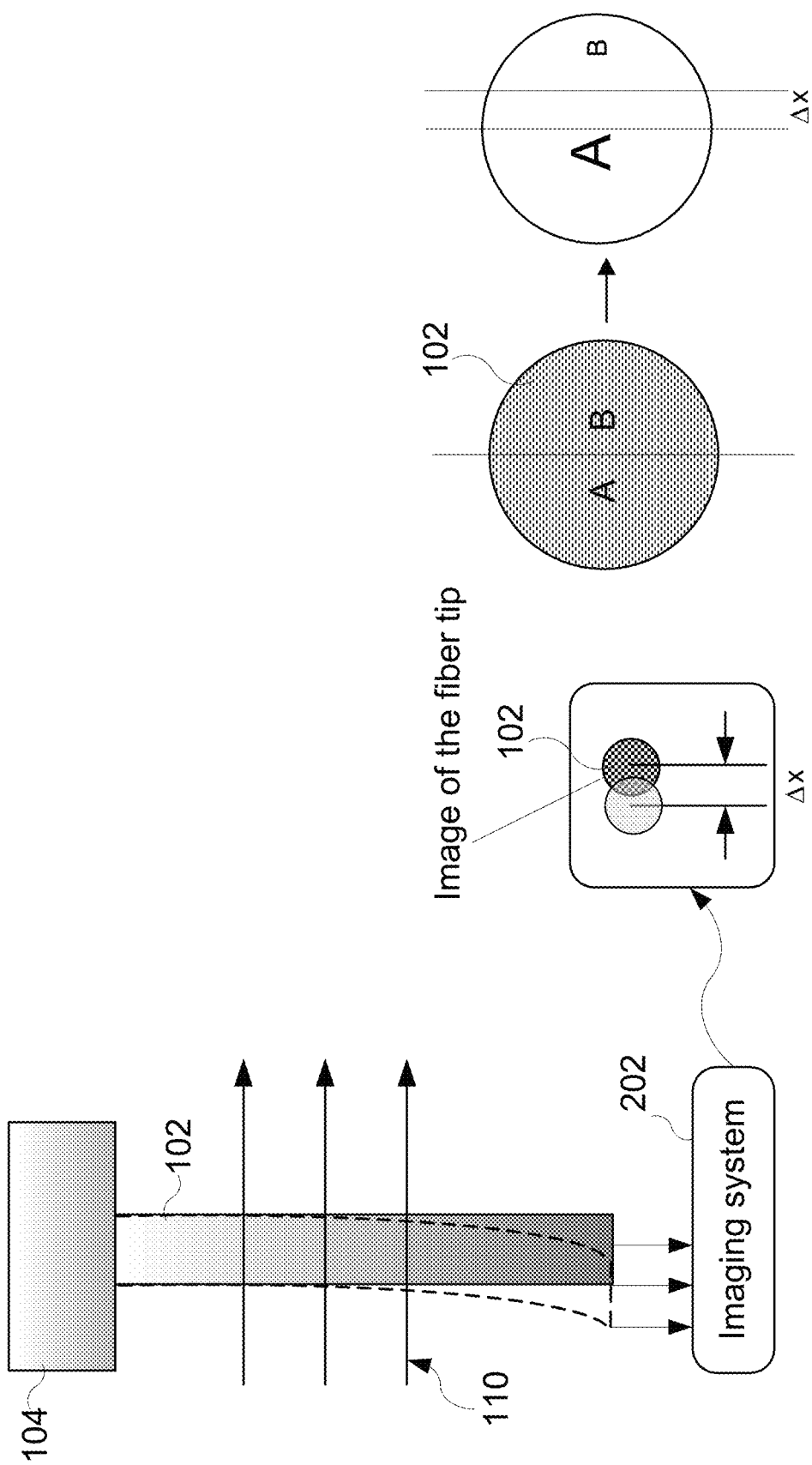
FIGS. 2A, 2B, and 2C are illustrations of a fiber positioned over an imaging system for detecting movement of the fiber before and after exposure to a sample.

In one implementation, differential optical detection is used to detect movement of fiber 102. FIGS. 2A and 2B are illustrations of fiber 102 positioned over imaging system 202 for detecting movement of fiber 102 before and after exposure to a sample. FIG. 2A shows an elevational view of fiber 102, while FIG. 2B shows a view of the tip of fiber 102 as taken from the perspective of imaging system 202 shown in FIG. 2A.

Imaging system 200 may include a CCD, CMOS or other imaging sensor configured to accurately record a position of fiber 102. In the system configuration shown in FIGS. 2A and 2B, imaging system 202 is positioned below fiber 102 and is oriented upwards. In that configuration, imaging system 202 images the tip of fiber 102 with a view oriented along the length of fiber 102. Accordingly, imaging system 202 views fiber 102 as a circle, as shown in FIG. 2B. Imaging system 202, therefore, captures movement of fiber 102 as movement of the circle depicted in FIG. 2B through imaging system 202's field of vision. Specifically, imaging system 202 captures a first image of fiber 102 before application of electric field 110, but after fiber 102 is exposed to the sample material. Imaging system 202 then captures a second image of fiber 102 after fiber 102 is exposed to electric field 110. A processor, either disposed within or external to imaging system 202, compares the two images to determine an amount of movement or displacement of fiber 102 after exposure to electric field 110. The processor can then use that displacement to characterize the sample material, as described above.

In one implementation, imaging system 202 is configured to divide each of the before and after images into two separate regions using a fixed line formed perpendicularly to the displacement direction (see, for example, regions A and B shown in FIG. 2C). The line defining the two separate regions is positioned to pass through the center of the image of fiber 102 when fiber 102 is in a resting position (i.e., with no application of electric field 110). At rest, the measured visual intensities (I) in regions A and B of fiber 102 are substantially the same. When fiber 102 is displaced, the intensities of each region changes as the area of each region has changed. As shown in FIG. 2C, at rest, regions A and B are substantially the same size. But when fiber 102 is displaced, as shown in FIG. 2C, the area of region A is larger than that of region B.

Accordingly, in this implementation, imaging system 202 is configured to constantly monitor the intensities of regions A and B as fiber 102 is exposed to electric field 110. Then imaging system 202 compares the relative size of region A and region B, and uses the resulting comparison to determine an amount of displacement of fiber 102. In one implementation, the comparison of the relative sizes of regions A and B is expressed as $(I_A-I_B)/(I_A+I_B)$, where $I_A$ and $I_B$ are the measured visual intensities of regions A and B, respectively. That ratio can then be translated into a displacement of fiber 102 using equation (4).

$$\Delta x = b \frac{I_A - I_B}{I_A + I_B} \quad \text{Equation (4)}$$

In equation (4), b is a calibration factor that may be determined experimentally.

This displacement-detection method is relatively simple to implement. Additionally, the method is setup to cancel common visual noise arising in both regions A and B in the image of fiber 102. In one implementation of this displacement-detection method, the tip of fiber 102 oriented towards imaging system 202 is etched to a sharp point in order to create a diffraction-limited spot in the image to assist in imaging.

In other implementations, rather than rely on the changing areas of different regions of fiber 102, imaging system 202 may instead identify a central intensity point of the images of fiber 102 in both the before and after images. The movement of that central intensity point can then be used to determine displacement of fiber 102. In such an approach, the displacement may be calculated according to equation (5).

$$\Delta x = \frac{\int xI(x, y)dxdy}{\int I(x, y)dxdy} \quad \text{Equation (5)}$$

When implementing the central intensity point analysis (for example, using CCD or CMS imaging devices), the integrals shown in equation (5) are replaced by summations performed over the pixels depicting the tip of fiber 102 in the before and after images.

These optical-displacement methods can be implemented using a conventional optical microscope equipped with a CCD or CMOS imager. Alternatively, the system may utilize positive sensitive or bicell photodiodes to detect fiber 102 displacement.

In other implementations, imaging system 202 may simply attempt to identify a center pixel of the before and after images of fiber 102 in order to determine the fiber 102's displacement.

Figure 3:
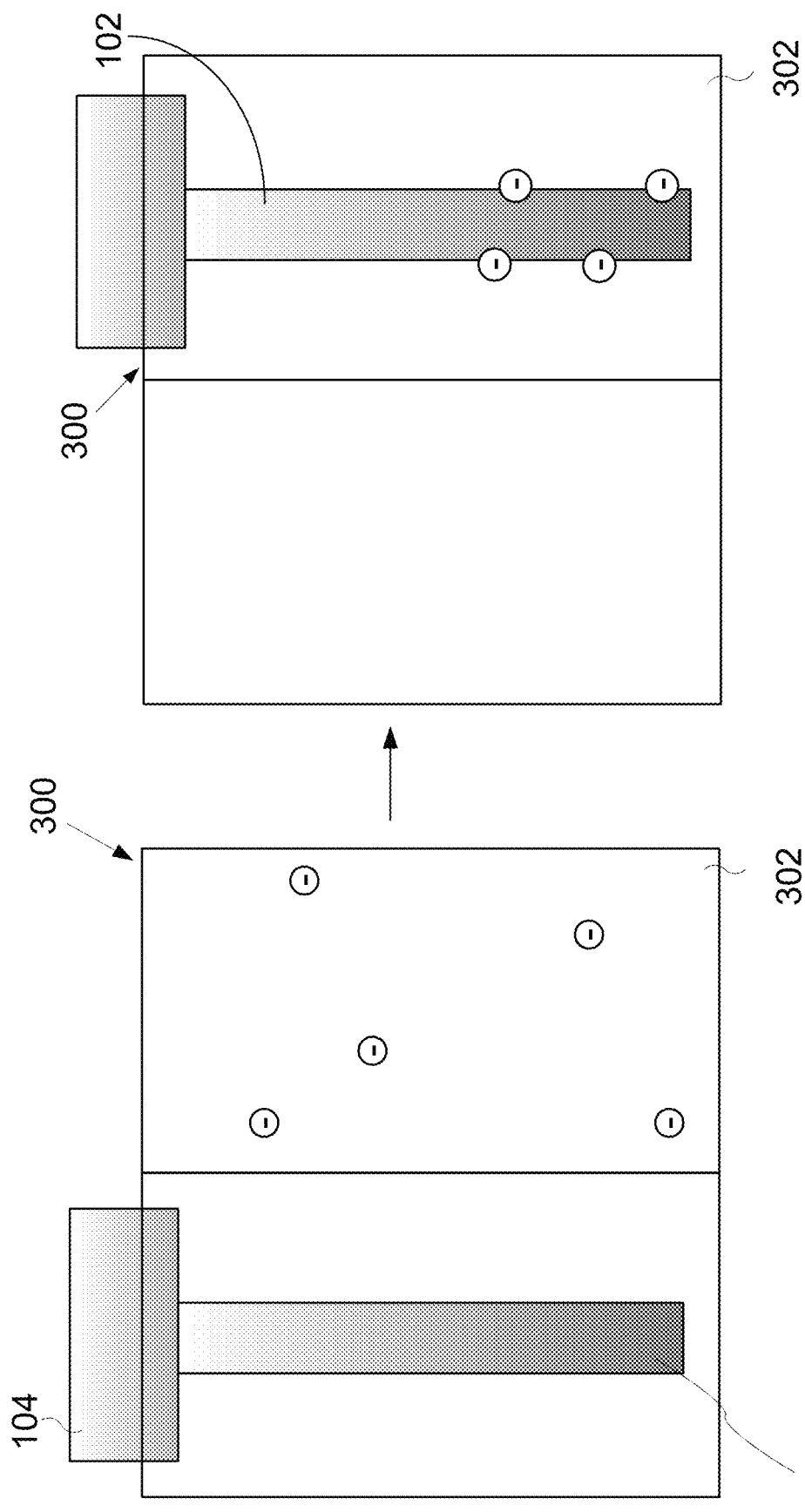
FIGS. 3A and 3B depict fiber 102 being disposed within a well of a microplate according to an embodiment.

The present system is compatible with conventional microplates (e.g., 96-well or 364-well microplates) that may be used to contain the sample material to be tested. For example, FIGS. 3A and 3B depict fiber 102 being disposed within well 302 of microplate 300. Fiber 102, or support 104 of fiber 102, may be connected to a robotic arm that is configured to place fiber 102 into well 302 for testing a sample material disposed therein. If the sample contains molecules of interest, those molecules can then interact with fiber 102 to generate a charge along the surface of fiber 102. After disposing fiber 102 into the sample material, the robotic arm could then position fiber 102 in front of an imaging system. The imaging system can be used to detect a movement of fiber 102 before and after the application of an appropriate electric field to fiber 102. In this arrangement, the present system takes advantage of established robotic and microplate handling capabilities for both high throughout and accurate screening of molecules for drug discoveries and for other applications.

The present system can be used in both in situ and ex situ implementations. For in situ applications, fiber 102 is inserted into solution wells, as shown in FIGS. 3A and 3B. This arrangement allows for analysis of the kinetics of molecular interactions and binding processes. This in situ application provides kinetic information, which is important for various applications. In that arrangement, though, the presence of an aqueous solution in which the sample material is suspended may screen or reduce the electric field applied to fiber 102 by the analysis system, which could decrease the fiber 102's deflection, making detection of movement of fiber 102 more difficult. To minimize the damping effect of the aqueous solution, fiber 102 may be withdrawn from the aqueous solution (and sample material) for testing. This allows for detection of fiber 102 bending, while fiber 102 is disposed in air, rather than the aqueous solution. In that case, because there is no aqueous solution to dampen movements of fiber 102 or the application of the electric field, fiber 102 will bend further, allowing for easier detection of fiber 102 bending. This implementation, though, does not allow for the collection of kinetic information, but may be useful for applications that do not require quantitative analysis. Depending on the specific need of the each application, therefore, either in situ or ex situ measurements can be carried out using the present system.

Figure 4:
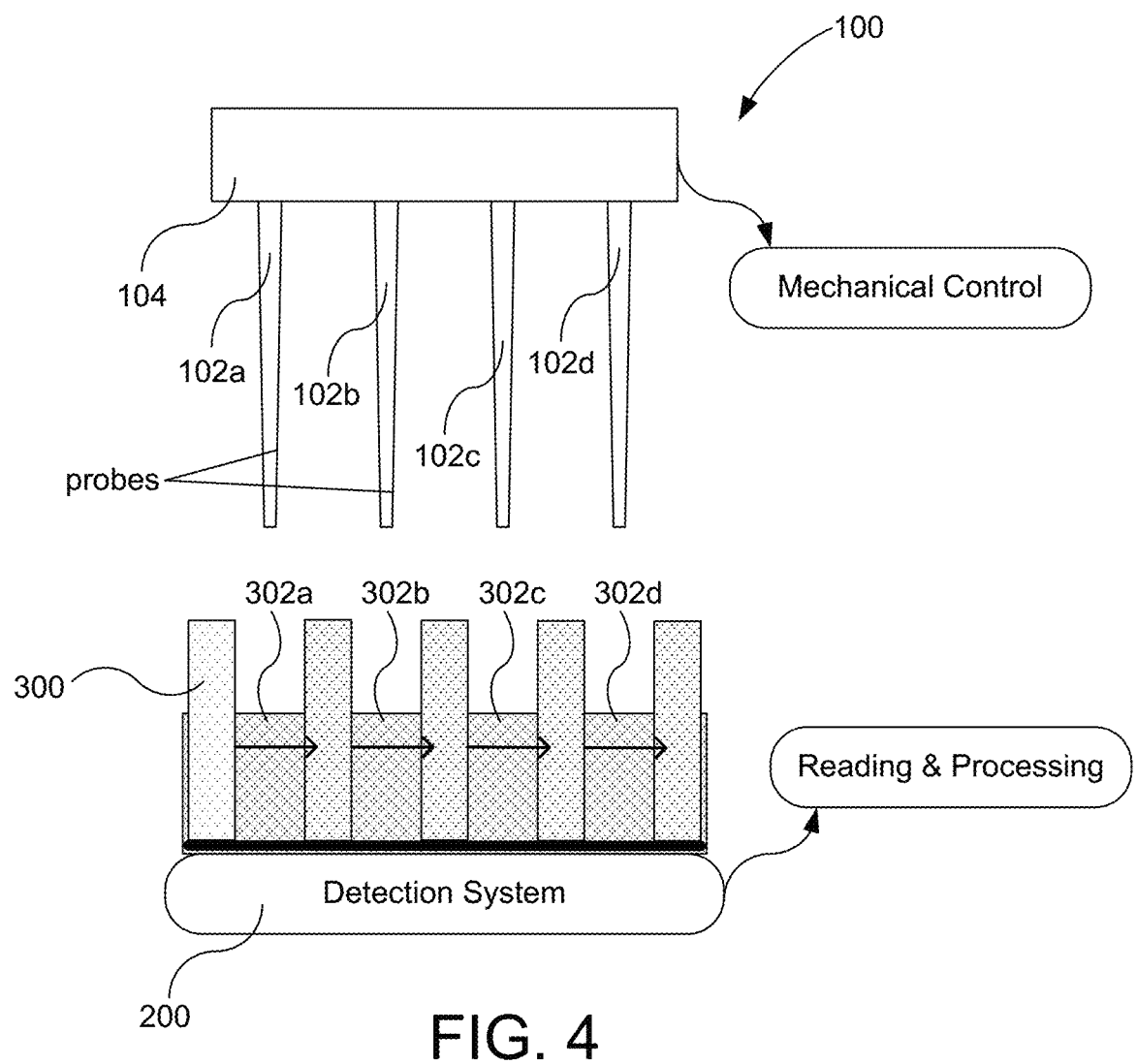
FIG. 4 shows an implementation of a system incorporating a number of fibers.

To increase throughput of the present system, multiple, separate, fibers 102 may be integrated into a single testing system. Each fiber 102 can then simultaneously test different wells in a microplate. FIG. 4, for example, shows an implementation of system 100 incorporating a number of fibers 102. Fibers 102 are spaced along support 104 to correspond with the positioning of wells 302 of microplate 300. Each of fibers 102 can then be dipped into wells 302 of microplate 300 to test material disposed therein. Imaging system 202 is positioned below wells 302 and is configured to separately image each one of the tips of fibers 102 to detect a displacement of fibers 102 before and after application of an appropriate electrical field. In the implementation shown in FIG. 4, each of fibers 102 may be mounted to support 104 which is, in turn, connected to a robotic arm that is configured to maneuver fibers 102 with respect to microplate 300.

As described above, the present system finds utility in any application calling for the detection of a particular substance or molecule within a sample material. The following illustrates some example, specific, uses of the system. The following listing should not be considered limiting in any way, and only serves to illustrate potential uses of the present system.

Phosphorylation is the addition of a phosphate ($PO_4^{3-}$) group to a protein or other organic molecule. It activates or deactivates many protein enzymes. Protein phosphorylation plays a significant role in a wide range of cellular processes, and has been the subject of a very large body of research. Detection of phosphorylation is difficult for the current detection technologies because the phosphate is small. The present system, therefore, may be used to detect phosphorylation and dephosphorylation because the chemical reaction is accompanied by a change in charge that can be accumulated on an appropriately sensitized fiber.

Another example application involves DNA sequencing. DNA sequencing by synthesis is an important approach for decoding DNA. It also involves phosphorylation, so the present invention can also be used as a readout method for DNA sequencing.

The present system may also be used to screen drugs that target phosphorylation receptors. The system can detect any molecules that change charges or partial charges. Examples include hormones and peptides, si-RNA and DNA hybridization.

As described herein, the present system is sensitive, allowing for detection of even single electron charges. Compared to mass-based label-free detection, the prevent system is sensitive only to charge changes, which minimize non-specific absorption issue. Additionally, the present system is compatible with microplate technology, facilitating quick adaption of the technology, high throughput screening while removing the need of microfluidics. The system is also compatible with conventional optical microscope, making the system easier to be accepted by users.

Figure 5:
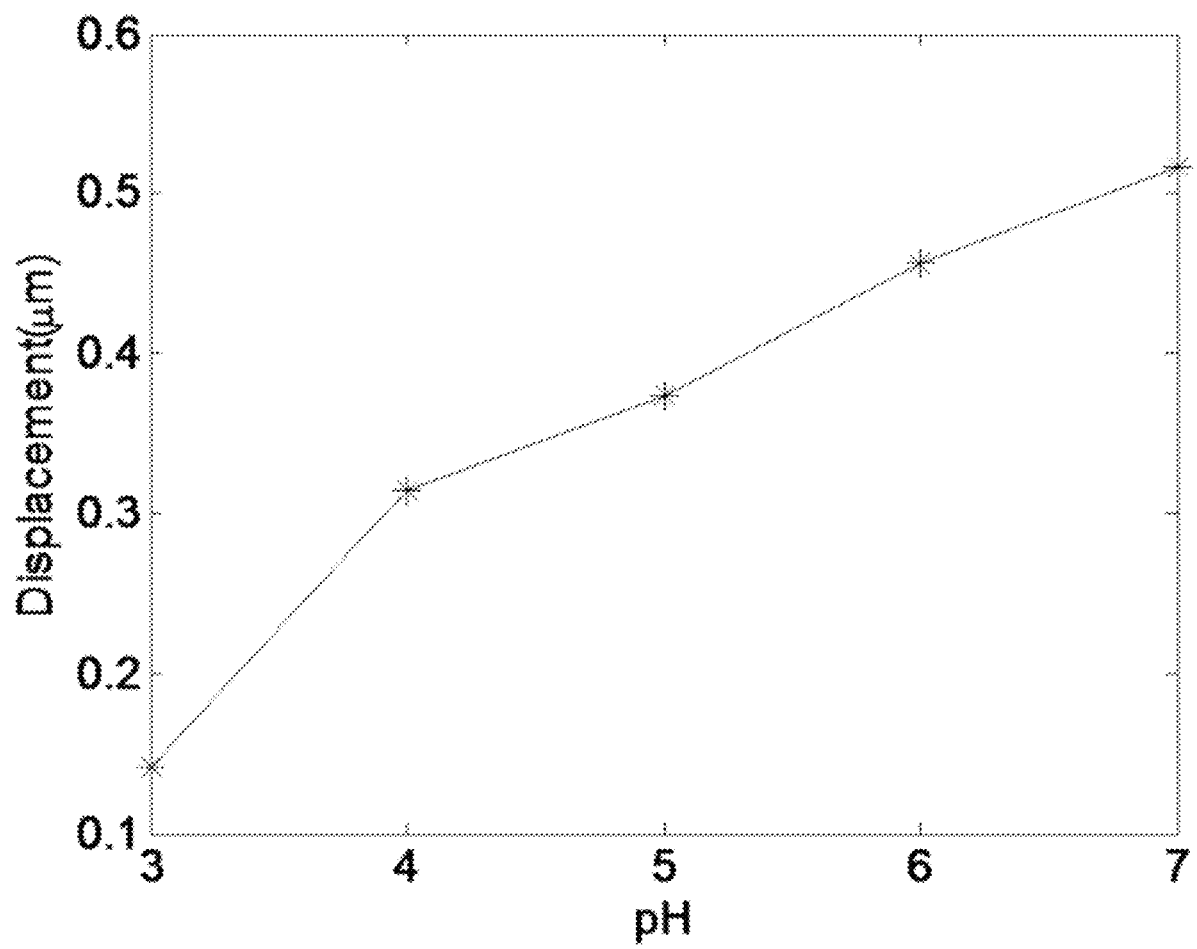
FIG. 5 is a graph showing experimental results for the present system illustrating a comparison of a pH level within a sample material to a corresponding displacement distance of a fiber after exposure to the sample material.

FIG. 5 is a graph showing experimental results for the present system illustrating a comparison of a pH level within a sample material to a corresponding displacement distance of fiber 102 after exposure to the sample material. As shown by FIG. 5, as the pH of a particular sample increases, the charge change on fiber 102 increases, resulting in a greater displacement of fiber 102 and facilitating detection by a fiber 102 displacement-monitoring system, such as the optical system described above.

The materials and methods described above are not intended to be limited to the embodiments and examples described herein.

The invention claimed is:

1. A system for analyzing a sample comprising small target molecules in a solution, the system comprising:
   a mechanical support coupled to an optical fiber sensitized to the small target molecules in the solution;
   at least two electrodes positioned on opposing sides of the optical fiber and configured to expose the fiber to a modulated electric field modulated at a given frequency;
   a sensor operably positioned and that is configured to detect both an amplitude of oscillation of the optical fiber at the given frequency of the modulated electric field and a direction of its displacement;
   wherein said sensor is further configured to use said amplitude of oscillation of the optical fiber at the given frequency of the modulated electric field and the direction of its displacement to characterize the sample for a presence or absence of said small target molecules in the solution,
   wherein the modulated electric field minimizes electrochemical reactions and allows the use of noise reduction methods to remove noise and drift issues.

2. The system of claim 1, wherein said sensor comprises position sensitive or bicell photodiode.

3. The system of claim 1, wherein said sensor comprises a mechanical sensor.

4. The system of claim 3, wherein said mechanical sensor is a pressure sensor.

5. The system of claim 1, wherein said sensor is an optical sensor.

6. The system of claim 1, wherein the optical fiber comprises a plurality of filaments.

7. The system of claim 6, wherein a first one of the plurality of filaments is sensitized to a first type of small target molecules in a solution, and a second one of the plurality of filaments is sensitized to a second type of small target molecules in a solution.

8. The system of claim 1, including a microplate comprising a plurality of wells, wherein said fiber is disposed within a well of said microplate.

9. The system of claim 1, wherein said sensor is further configured to perform a Fourier transform.

10. The system of claim 8, wherein the mechanical support is coupled to at least two optical fibers sensitized to the small target molecules in the solution, and each of said at least two optical fibers is disposed in a different well of said plurality of wells.

11. The system of claim 1, wherein the optical fiber comprises glass, metal, or carbon.

12. The system of claim 1, wherein the system is configured to lessen electrochemical reactions of the solvated target molecules by limiting the given frequency of the modulated electric field to more than 1 Hz.

\* \* \* \* \*